United States Patent [19]
Glastra

[11] Patent Number: 5,344,444
[45] Date of Patent: Sep. 6, 1994

[54] EXPANDABLE RING, CYLINDER OR SLEEVE WHICH CAN BE MADE NON-DEFORMABLE

[75] Inventor: Hendrik Glastra, Enschede, Netherlands

[73] Assignee: Industrial Research B.V., Netherlands

[21] Appl. No.: 909,051

[22] Filed: Jul. 2, 1992

[30] Foreign Application Priority Data

Jul. 3, 1991 [NL] Netherlands .......... 9101159

[51] Int. Cl.$^5$ .............................................. A61F 2/06
[52] U.S. Cl. ...................................................... 623/1
[58] Field of Search .................. 623/1, 12; 606/192, 606/194, 195; 602/8

[56] References Cited

U.S. PATENT DOCUMENTS 3,415,243  12/1968  Sheldon ................................. 602/8
5,100,429  3/1992  Sinofsky et al. .................... 606/195

FOREIGN PATENT DOCUMENTS 0428479  5/1991  European Pat. Off. .
8001460  7/1980  PCT Int'l Appl. .
9001969  3/1990  PCT Int'l Appl. .

OTHER PUBLICATIONS

Physics for Scientists & Engineers, Second Edition, Serway Saunders Golden Sunburst Series, Saunders College Publishing Philadelphia, Pa. 19105, 1986 p. 1002.

Primary Examiner—Jerome L. Kruter

[57] ABSTRACT

A stent made of a hollow expandable ring or sleeve is inserted into a body vessel to locally support or strengthen the vessel. The stent includes a compartment filled with a curable material. The stent is fixed to an inflatable balloon and positioned within the vessel at the desired location. When the balloon is inflated, the stent is expanded into a desired shape. A light conducting fiber is introduced into the vessel to irradiate the material to cure the material in the stent, such that the stent retains the desired shape even after the balloon is removed from the body vessel.

11 Claims, 5 Drawing Sheets

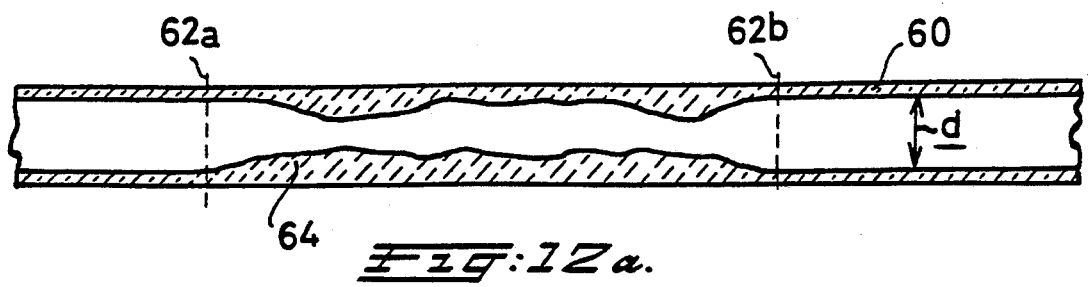
_Fig. 12a._
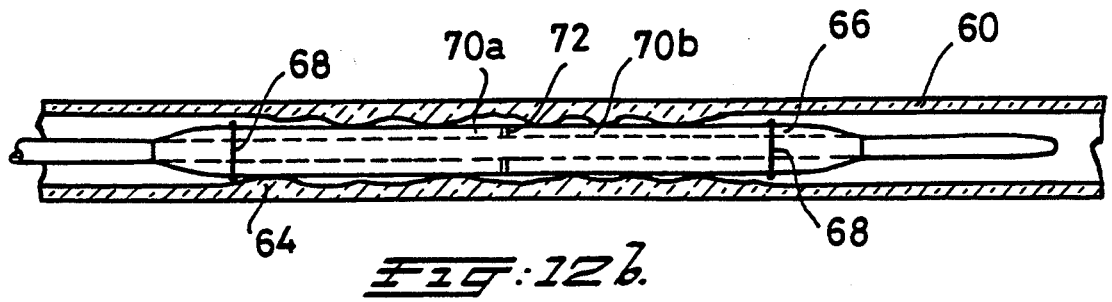
_Fig. 12b._
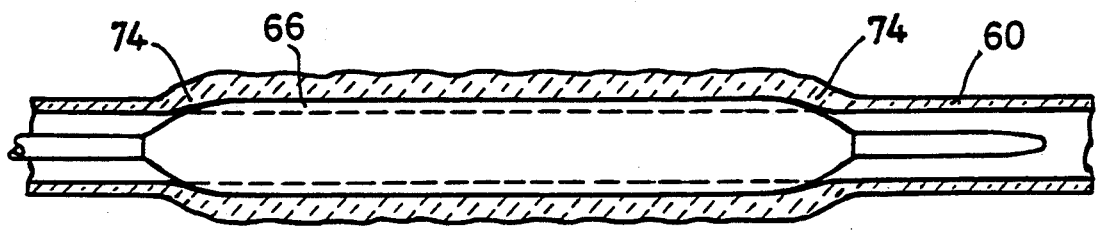
_Fig. 12c._
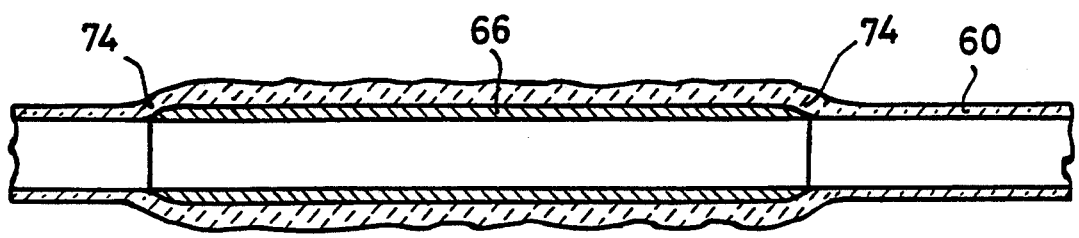
_Fig. 12d._

EXPANDABLE RING, CYLINDER OR SLEEVE WHICH CAN BE MADE NON-DEFORMABLE

BACKGROUND OF THE INVENTION

The invention relates to an expandable ring or cylinder, particularly for locally supporting or strengthening a body vessel, comprising an expandable body being able to retain its expanded shape after its introduction at the desired location.

DESCRIPTION OF THE PRIOR ART

Such a device, particularly with a cylinder shape and commonly called a "stent" is known from EP-A-0 428 479. This document proposes the use of a hollow body which is made up of a plastic material having such properties that it can be elastically deformed when heated at a temperature of about 75° C. The body is placed around a heatable dotter balloon which is brought to the desired place, whereafter the dotter balloon is heated and inflated so that the plastic material of the body softens and expands with the balloon; then, when the heating is ended and the body cools off it is expected to retain its shape.

This known device has several drawbacks. The first one is that in the solid state the hollow body is rigid so that there is a real risk of damaging the vessels through which it has to pass so that the treatment can cause severe suffering to the patient. The second drawback is that there is a very limited source of materials from which the hollow body can be made: it must be softened when heated and become solid again after cooling-off while at the same time it must be compatible with the body environment as it remains in the body. Of course another severe drawback is the fact that the body must be heated to a temperature which lies considerably above the body temperature of the patient. Furthermore the very nature of the rigid material used limits the extent to which it can be expanded.

SUMMARY OF THE INVENTION

The present invention aims to obviate the drawbacks of the prior art. According to the present invention the body of the ring or sleeve is hollow and contains a curable plastic material which can cure after positioning and thus assures that the desired expanded shape is retained.

With the present invention, the body of the stent is very soft and pliable before curing of the curable materials therein, so that the introduction will not be much more difficult than the known "dotter" balloon treatment. Also, there will be no objectionable temperature rise. The final shape can be rigidly controlled and adapts itself easily to the vessel in which it is inserted. The device according to the invention can thus be used much more universally than the known devices.

Preferably the hollow body of the ring or sleeve is divided into at least two compartments which are separated from each other by at least one partition which can be broken, the compartments each being filled with a first and a second substance respectively, the mixing together of which leads to a reaction resulting in curing of the produced mixture.

Preferably the partition has such a configuration that, when the diameter of the element is increased, a passage is opened between the compartments.

When the curing material is the kind in which curing starts a predetermined period after mixing of the components, the partition(s) in the ring or sleeve can be broken outside the patient's body, before treatment starts, because the time necessary for reaching the desired location in the body can be determined with a good approximation on the basis of a scan of the patient's body.

Preferably the shape makes it possible to hold the ring or sleeve around an uninflated dotter balloon or like device during the insertion thereof in a body vessel, for instance because it is spirally wound around the uninflated dotter balloon. The ring or sleeve can be fixed to the dotter balloon or like device by means of threads which break when the dotter balloon or device is inflated.

Finally the curable material an be of the kind in which curing is started or accelerated under the influence of radiation with a suitable wave length, for instance UV light. This radiation can be transmitted to the curable material by a light conducting fiber from an outside source.

DESCRIPTION OF THE DRAWINGS

The invention is explained with reference to the drawings, in which:

FIGS. 12a–12d show several stages of the treatment of a body vessel having a constriction of considerable length.

DESCRIPTION OF PREFERRED EMBODIMENTS

Figure 1:
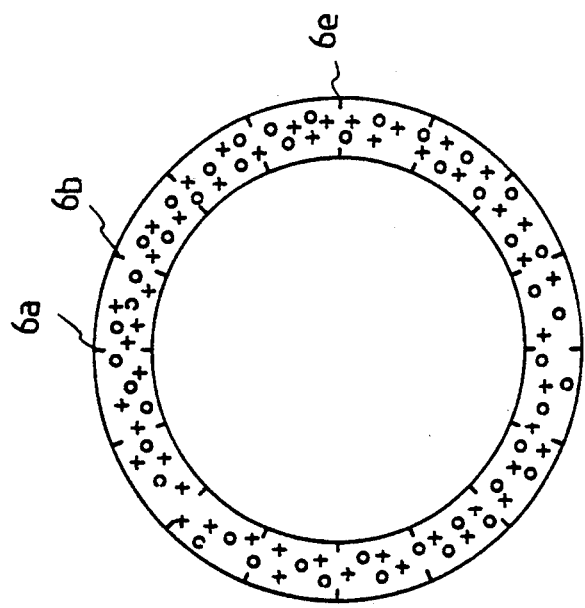
FIG. 1 is a longitudinal section of a ring of the first embodiment of the invention, in a non-expanded state.

In FIG. 1 reference numeral 2 indicates an expandable supporting ring according to the invention, comprising a closed tubular element 4 which is divided by partitions 6a–6p into a number of compartments 8a–8p. Each of these compartments is filled with one of two chemical substances which differ from each other and on mixing undergo a reaction which leads to the curing of the resulting mixture. The compartments marked with a cross (+) are filled with the first substance, while the compartments marked with a dot (.) are filled with the second substance. It is possible to use, for example, an epoxy resin curing system in which the first substance is an epoxy resin, for example Shell's EPIKOTE ®, combined with a suitable amine curing agent as the second substance; the reaction taking place between these substances leads at body temperature to complete curing of the resulting mixture within a few minutes, so that the fitting can take place quickly and the patient suffers as little discomfort as possible. Another suitable combination is an unsaturated polyester as the first substance and benzoyl peroxide catalyst as the second substance. Use can also be made of a diisocyanate compound as the first substance and water or a water-containing solvent as the second substance. Even the use of the component parts of plaster of Paris (lime and water) is conceivable. For other suitable combinations reference is made to "Handbook of Composites", George Lubin, published in 1982 by Van Nostrand Reinhold Company Inc.

Figure 3:
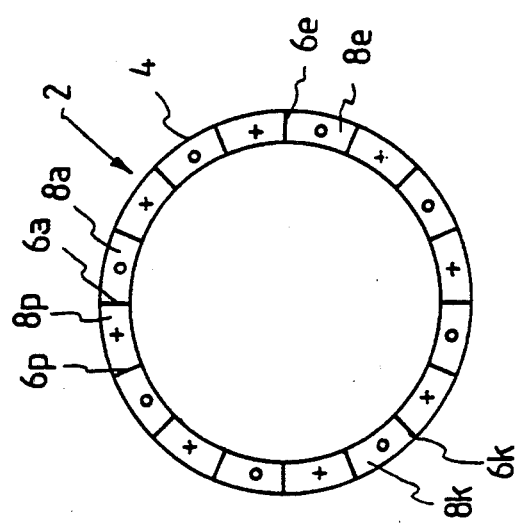
FIG. 3 is a longitudinal section of the ring of the first embodiment, in an expanded state.
Figure 2:
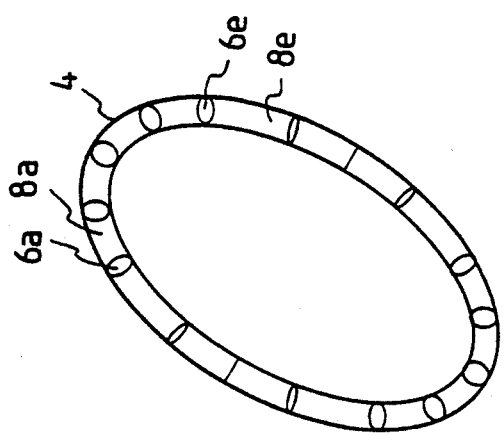
FIG. 2 is a perspective view of the ring of the first embodiment.

When the diameter of such a ring, shown in perspective in FIG. 2, is enlarged in a suitable manner from within, shown in FIG. 3, the respective partitions 6a–6p are stretched and broken through, so that the substances present in the compartments 8a–8p are mixed together, with the result that the curing reaction then occurring leads to a non-deformable, solid ring which permanently retains the shape acquired.

Figure 6:
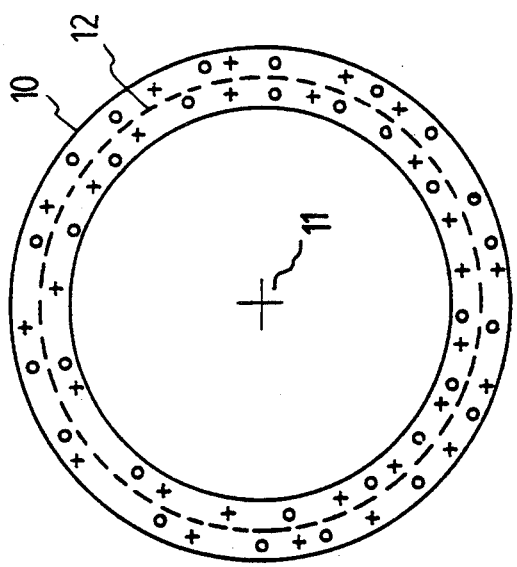
FIG. 6 is a longitudinal section of the ring of the second embodiment, in an expanded state.
Figure 5:
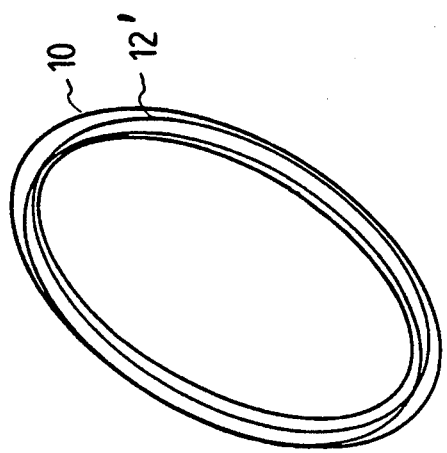
FIG. 5 is a perspective view of the ring of the second embodiment.
Figure 4:
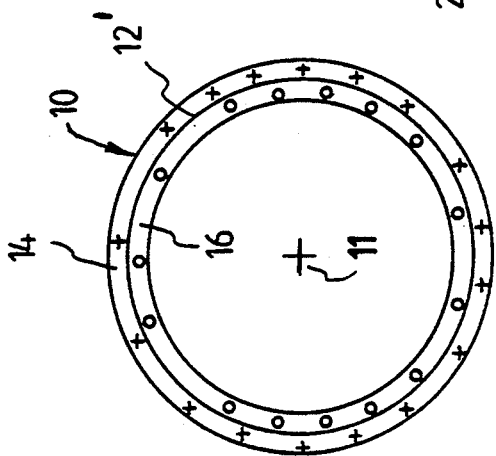
FIG. 4 is a longitudinal section of a ring according to a second embodiment of the invention, in a non-expanded state.

FIG. 4 shows a longitudinal section through a ring of a second embodiment according to the invention; this embodiment is shown in perspective in FIG. 5 and in an expanded state in FIG. 6. The ring 10 is divided, by a circular partition 12 running parallel to the central axis 11, into two concentric compartments 14 and 16, of which the compartment 14 is filled with the first substance, and the compartment 16 is filled with the second substance. FIG. 6 shows how upon expansion of the ring 10, the partition 12 is broken through and the two substances quickly mix together over the entire periphery of the ring.

Figure 7:
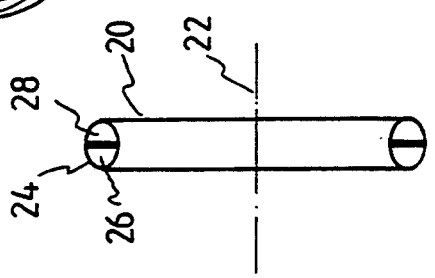
FIG. 7 is a cross-section of another embodiment of a ring according to the invention.

FIG. 7 shows in cross-section an embodiment in which the ring 20 is divided into the two compartments 26 and 28 by a partition 24 running all the way around the ring at right angles to the central axis 22. When partition 24 is broken, the substances in compartments 26 and 28 admix in a corresponding way to that which is described above.

Figure 8:
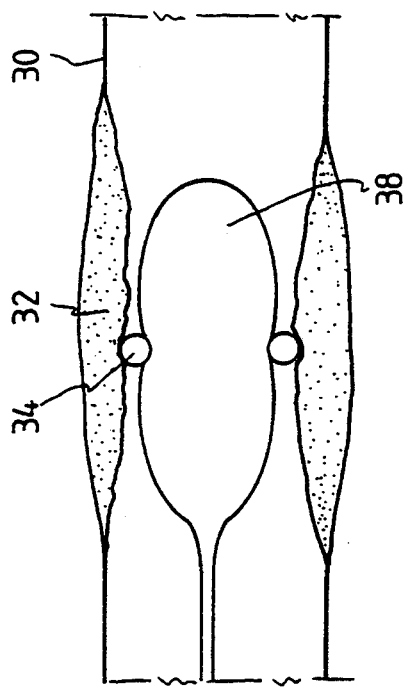
FIG. 8 is a longitudinal section through a part of a blood vessel containing an expandable ring according to the invention, in the state prior to its expansion.
Figure 9:
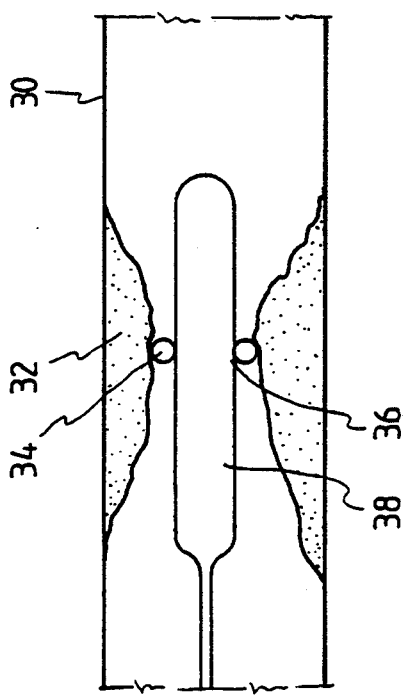
FIG. 9 is a longitudinal section according to FIG. 8, with the ring expanded and the inflatable balloon still present.
Figure 10:
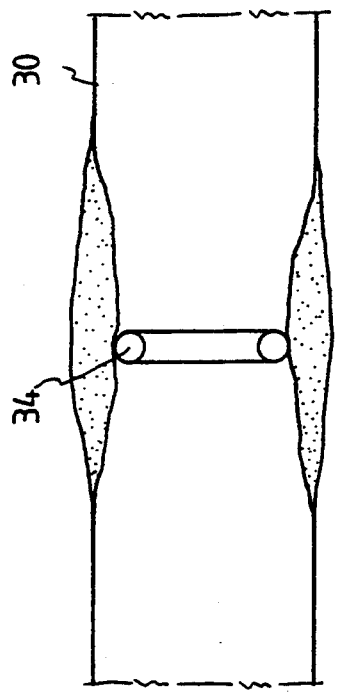
FIG. 10 is a longitudinal section through the blood vessel configuration after the balloon has been removed and the ring positioned in place.

FIG. 8 shows the way in which a ring according to the invention can be used. The figure shows in cross-section a blood vessel 30 with a local constriction 32. The ring 34 is fitted by means of a suitable instrument at this point, and an inflatable balloon 38 is introduced into the hollow space 36 within the ring, for example a balloon used in the so-called "dotter-balloon" treatment. As FIG. 9 illustrates, the balloon is inflated, with the result that the ring 34 expands, thus compressing the constriction 32. Within a few minutes of the breaking of the partitions in the ring, the chemical reaction between the respective substances present in the compartments of the ring is completed and the ring 34 has permanently acquired the configuration shown in FIG. 10. The balloon 38 can be withdrawn and the constriction of the vessel 32 is permanently mended.

Figure 11:
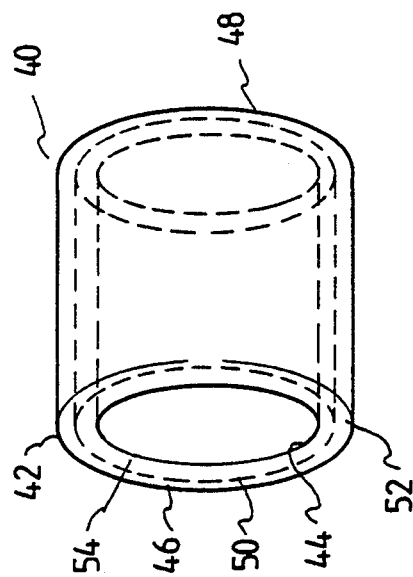
FIG. 11 shows schematically a sleeve-shaped device according to another embodiment of the invention.

FIG. 11 shows the expandable element in the form of a sleeve-shaped configuration 40, comprising an outer wall 42, an inner wall 44, end walls 46 and 48, and a partition 50 which divides the sleeve into two compartments 52 and 54. A blood vessel or organ can be supported over a greater length with such an expandable element.

FIG. 12a shows how a body vessel 60, particularly a blood vessel has, between the points 62a and 62b, a number of constrictions 64 which considerably affect the flow of body fluid. By means of a body scan the distance between the points 62a and 62b is determined and then a stent or sleeve according to the present invention is chosen which has a length long enough to cover the distance. Furthermore the free diameter d of the body vessel is also determined and a stent is chosen with such a diameter that, when it is brought into position and the dotter balloon is inflated, the stent is pressed into the body vessel in such a way that after the curing of the components a smooth transition between the unrestricted part of the vessel and the stent is obtained.

FIG. 12b shows the dotter balloon device and the stent 66 according to the invention, the stent or sleeve being fixed to the dotter balloon with surgical thread 68. The stent 66 is divided into two compartments 70a, 70b separated by the partition 72. Partition 72 can be broken before the dotter balloon is inserted into the body vessel or can be of the kind which breaks when the dotter balloon is inflated. The inflated balloon is shown in FIG. 12c, wherein the stent 66 is pressed into the wall of the vessel 60 to such an extent that there are smooth transitions 74 between the wall of the unrestricted parts of the vessel and the inner diameter of the stent 66.

After curing of the component materials in the stent 66, the dotter device is retracted, and the stent 66 remains in the cured position in body vessel 60 as shown in FIG. 12d.

Figure 13:
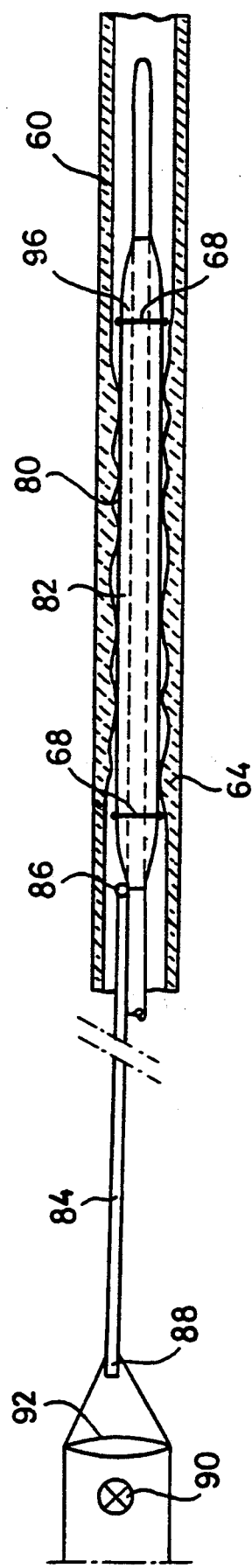
FIG. 13 shows another embodiment according to the invention.

FIG. 13 shows the use of a stent 80 according to another embodiment of the invention, having only one compartment 82 which is filled with a mixture of materials. Curing starts when the mixture is irradiated with radiation of a suitable wave length, particularly UV light. As described above, stent 80 is fixed by means of surgical threads 68 to the dotter balloon 96. Together with the dotter balloon 96 a light conducting glass fiber 84, having at one end a small lens 86, is inserted into the body vessel. When the lens 86 has reached the desired position, the other end 88 of fiber 84 is irradiated with ultra violet light from a suitable source 90, via a schematically shown focussing system 92. In this way a considerable amount of UV energy can be transmitted to the desired position, resulting in rapid curing of the curable material.

It is clear that countless variants are possible within the scope of the invention. For example, it is conceivable to fill the respective compartments with more than two different substances, while many variants are also possible in shape, size and cross-sectional configuration.

Applications other than the medical application described are, of course, also possible.

I claim:

1. A device for locally supporting and strengthening a body vessel, comprising:
   a hollow, expandable stent to be positioned in the body vessel, the stent containing curable material; and
   a light conducting fiber to be inserted into the body vessel for transmitting radiation from an outside source to the curable material, wherein, when the material is irradiated with a suitable wavelength, curing is started or accelerated and the material is cured, such that the stent retains a desired shape in the body vessel.

2. The device of claim 1, wherein the stent is fixed to an inflatable balloon prior to insertion in the body vessel.

3. The device of claim 2, wherein the stent is fixed to the balloon by surgical threads which break when the balloon inflates.

4. The device of claim 2, wherein the stent is spirally wound around the inflatable balloon prior to insertion in the body vessel.

5. The device of claim 1, wherein the radiation comprises ultraviolet light.

6. A method for locally supporting and strengthening a body vessel, comprising the steps of:
   positioning a hollow, expandable stent in the body vessel, the stent containing curable material;
   expanding the stent into a desired shape in the body vessel; and
   transmitting radiation to the curable material through a light conducting fiber for curing the material, such that when the material is irradiated with a suitable curing is started or accelerated and the material is cured, such that the stent retains the desired shape in the body vessel.

7. The method of claim 6, wherein the steps of positioning the stent in the body vessel and expanding the stent into a desired shape are carried out by fixing the stent to an inflatable balloon prior to inserting the stent in the body vessel, and then inflating the balloon after the stent is positioned in the body vessel, such that the stent is expanded to the desired shape in the body vessel.

8. The method of claim 7, wherein the stent is fixed to the inflatable balloon with surgical threads.

9. The method of claim 8, wherein the surgical threads are broken when the balloon is inflated within the body cavity.

10. The method of claim 7, wherein the stent is fixed to the inflatable balloon by spirally winding the stent around the balloon.

11. The method of claim 6, further comprising the step of removing the light conducting fiber and the balloon from the body vessel, the stent remaining positioned in the desired shape within the vessel.

* * * * *